United States Patent [19]

Beach et al.

[11] Patent Number: 4,711,969

[45] Date of Patent: Dec. 8, 1987

[54] OLIGOMERIZATION OF ETHYLENE IN METHANOL AND WATER

[75] Inventors: David L. Beach, Kingwood, Tex.; James J. Harrison, Novato, Calif.

[73] Assignee: Chevron Research Company, San Francisco, Calif.

[21] Appl. No.: 900,204

[22] Filed: Aug. 25, 1986

[51] Int. Cl.$^4$ ................................................ C07C 2/32
[52] U.S. Cl. .................................... 585/511; 585/514; 585/515; 585/526; 585/527; 585/531
[58] Field of Search .............. 585/511, 526, 527, 514, 585/515, 531

[56] References Cited

U.S. PATENT DOCUMENTS

| | | | |
|---|---|---|---|
| 4,293,727 | 10/1981 | Beach et al. | 585/527 |
| 4,301,318 | 11/1981 | Beach et al. | 585/511 |
| 4,310,716 | 1/1982 | Beach et al. | 585/511 |
| 4,382,153 | 5/1983 | Beach et al. | 585/511 |

*Primary Examiner*—Asok Pal
*Attorney, Agent, or Firm*—S. R. La Paglia; T. G. DeJonghe

[57] ABSTRACT

A process for oligomerizing ethylene using a nickel ylide catalyst substituted with a sulfonato group, wherein the oligomerization is carried out in the presence of methanol and water.

28 Claims, 1 Drawing Figure

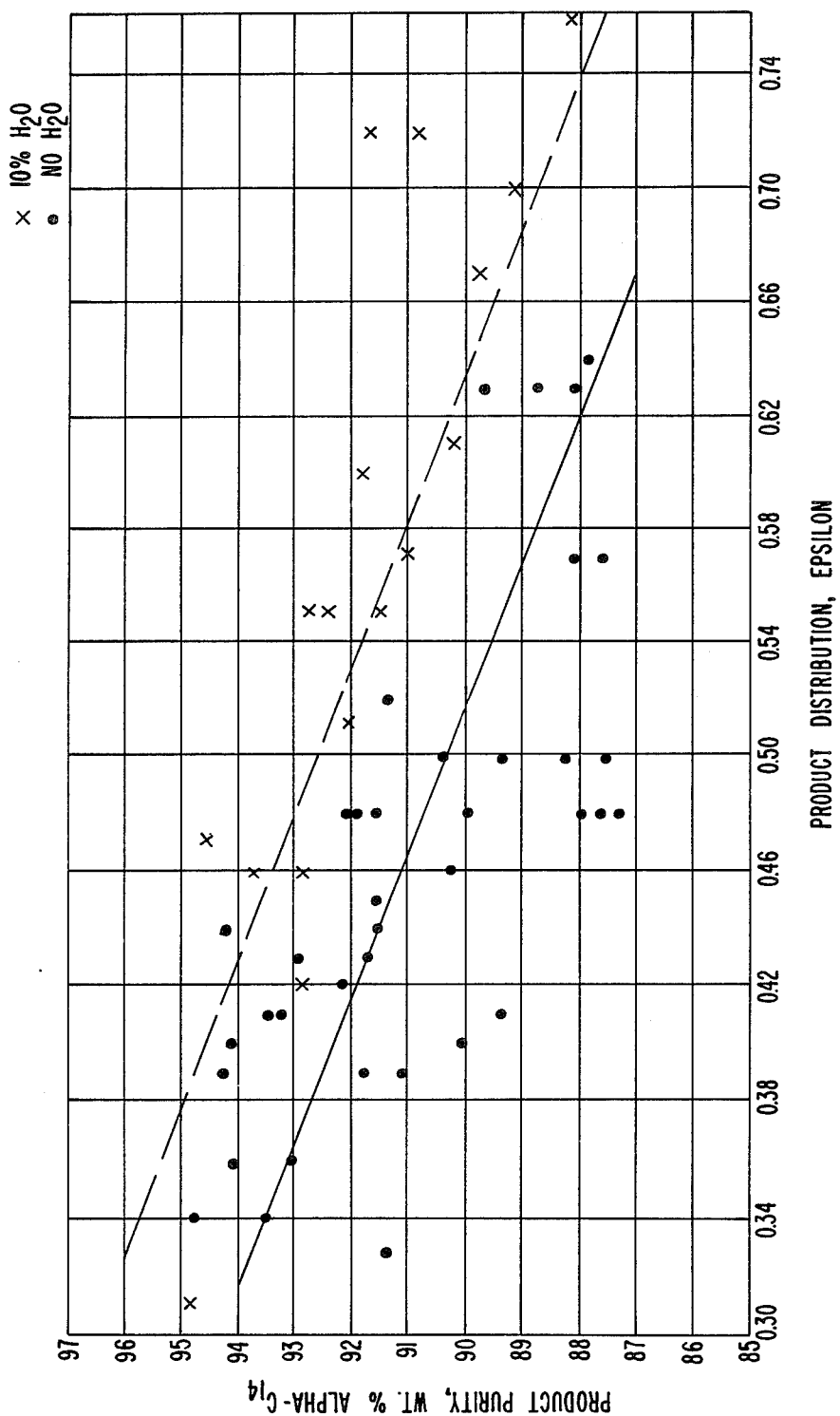

4,711,969

OLIGOMERIZATION OF ETHYLENE IN METHANOL AND WATER

CROSS-REFERENCES TO RELATED APPLICATIONS

Reference is made to Applicant's following U.S. Patents:

U.S. Pat. No. 4,293,502, Nickel Ylides, issued Oct. 6, 1981;

U.S. Pat. No. 4,293,727, Process for Oligomerization of Ethylene, issued Oct. 6, 1981;

U.S. Pat. No. 4,310,716, Process for Oligomerization of Ethylene in Methanol, issued Jan. 12, 1982;

U.S. Pat. No. 4,377,528, Group VA Salts and Process for Preparing Same, issued Mar. 22, 1983;

U.S. Pat. No. 4,377,529, Sulfonated Group VA Ylides and Process for Preparing Same, issued Mar. 22, 1983;

U.S. Pat. No. 4,382,153, Process for Oligomerization of Ethylene in Methanol, issued May 3, 1983; and U.S. Pat. No. 4,529,554, Process for the Preparation of Nickel Ylides Containing Ylide Ligands with a Sulfonated Group V Component, issued July 16, 1985.

FIELD OF THE INVENTION

The present invention relates to the use of nickel ylides to oligomerize ethylene in a solvent medium containing methanol.

DESCRIPTION OF THE PRIOR ART

It is well known in the art to use a variety of catalysts to oligomerize ethylene to higher molecular weight olefins. The term "oligomerize" has been employed, and is employed herein to describe the conversion of lower olefins such as ethylene to olefinic products of higher molecular weight, e.g., to dimer, trimer, tetramer and the like. The reaction rate and product distribution obtained are highly dependent on the exact catalyst composition and the reaction conditions employed. Two such general classes of catalysts are the "Ziegler" types consisting of aluminum trialkyls and the "Ziegler-Natta" types consisting of aluminum alkyls or alkyl halides and titanium halides. Major disadvantages of aluminum alkyl catalysts are their highly reactive and pyrophoric nature and the fact that they must be used at relatively high temperatures, e.g., 200° C. to 275° C. and pressures, e.g., 2000 to 4000 psig. Although much milder reaction conditions are used when the aluminum alkyls are used in conjunction with titanium halides, product quality and ease of catalyst separation from products of both of these prior art types of catalysts are not as high as desired.

An article by W. Keim, F. H. Kowaldt, R. Goddard and C. Kruger entitled "Novel Coordination of (Benzoylmethylene) triphenylphosphorane in a Nickel Oligomerization Catalyst", in Angew. Chem. Int. Ed. Engl. (1978) No. 6, page 466, discloses that a nickel ylide having the structure:

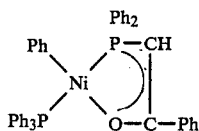

converts ethylene into alpha olefins or polyethylene.

SUMMARY OF THE INVENTION

According to the present invention, a process is provided for oligomerizing ethylene to normal alpha olefins, that is, straight chain alpha olefins, which process comprises reacting ethylene in a methanol-water mixture containing 0.5 to 20 wt % water under oligomerization conditions in contact with a nickel ylide defined by the following formula:

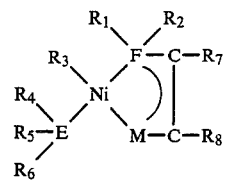

wherein $R_1$, $R_2$, $R_3$, $R_4$, $R_5$, $R_6$, $R_7$ and $R_8$ are either alike or different members selected from the group consisting of hydrogen, alkyl radicals having from about 1 to about 24 carbon atoms, aryl radicals having from about 6 to about 20 carbon atoms, alkenyl radicals having from about 2 to about 30 carbon atoms, cycloalkyl radicals having from about 3 to about 40 carbon atoms, aralkyl and alkaryl radicals having from about 6 to about 40 carbon atoms, halogen radicals, hydroxyl, alkoxy and aryloxy groups, and hydrocarbyl groups carrying halogen, hydroxyl, alkoxy or aryloxy groups, provided that at least one of each $R_1$ to $R_8$ radicals is a sulfonato group or an alkyl, aryl, alkenyl, cycloalkyl, aralkyl or alkaryl carrying a sulfonato group, M is sulfur or oxygen, E is phosphorus, arsenic, antimony or nitrogen and F is phosphorus, arsenic or antimony, to obtain a reaction product containing (A) a methanol-water phase having dissolved therein said nickel ylide and (B) an alpha olefin phase and then separating said phases from each other to recover said alpha olefin phase.

Preferred amounts of water used in the process of the present invention are between 2 and 15 wt % more preferably between 7 and 13 wt %. The weight percent water is calculated as a percent of the combined methanol and water which is fed to the reaction zone in the oligomerization process of the present invention.

Among other factors, the present invention is based on our finding that the addition of water to the reaction zone does not ruin the catalyst or its activity, particularly when the wt % water is controlled to below about 20 wt % of the combined methanol-water solvent. In addition, we have found that the water has an unexpectedly marked affect in improving the phase separation of the catalyst-rich phase from the product olefin-rich phase. Also we have found that the inclusion of water in the reaction zone results in a surprising increase in the purity of the alpha olefin product, and in a shift in product distribution toward lighter alpha olefin product.

Typically, in the process of the present invention, the ethylene, methanol, water and nickel ylide catalyst are fed to a reaction zone or a reactor, such as a continuous stirred tank reactor, wherein the oligomerization reaction is controlled by reaction conditions such as temperature, pressure, residence time and catalyst concentration. The reaction effluent is passed to a separation zone wherein a methanol-water catalyst phase is separated for recycle to the reaction zone, also ethylene is separated for recycle, and product alpha olefins are separated. The separation may be carried out in two steps. First, a gas/liquid separation wherein recycle ethylene gas is removed. In a second step, the liquid from the first step may be passed to a liquid/liquid separator where a methanol, water and catalyst phase are separated as a lower liquid phase for recycle to the reaction zone and an organic liquid phase is separated as a top or lighter phase. The organic phase, consisting of minor amounts of ethylene, but mainly of the product normal alpha olefins, is preferably passed to a recovery zone to recover additional ethylene for recycle to the reaction zone and to recover the product normal alpha olefins. The product alpha olefins will typically be primarily in the $C_4$ to $C_{30}$ range, but may range from $C_4$ to as high as $C_{100}$.

The catalysts used in the reaction zone are the nickel ylides as set forth in our prior patents, particularly including U.S. Pat. No. 4,310,716 and U.S. Pat. No. 4,293,502, the disclosures of which patents are incorporated herein by reference. The same catalysts which are preferred in those cited patents are preferred herein. Likewise, preferred catalyst preparation procedures including methods of including a sulfonate group in the catalyst, and preferred reaction conditions such as temperatures, pressures, catalyst concentration and residence time, are as described in the cited patents, especially U.S. Pat. No. 4,310,716 and U.S. Pat. No. 4,293,502.

Such preferred reaction conditions include a temperature between 20° C. and 100° C., oligomerization reaction zone residence time between 10 minutes and 24 hours, and pressures between 10 and 3000 psig, more preferably between 100 and 2000 psig.

BRIEF DESCRIPTION OF THE DRAWING

The drawing is a graph showing the effect of 10 wt % water on product $C_{14}$ alpha olefin.

EXAMPLES

Ethylene oligomerization reactions were carried out using a sulfonated nickel ylide (SUNY) catalyst. The SUNY catalyst used was Compound 9 of U.S. Pat. No. 4,310,716 which has the following structure:

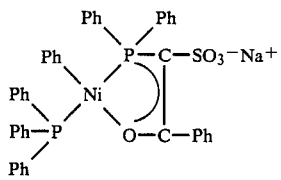

The SUNY catalyst was prepared in accordance with the Example III preparation of U.S. Pat. No. 4,310,716.

Results for experiments at various water levels are set forth in Table I below.

The experiments were performed using freshly prepared solutions of SUNY catalyst in methanol or a methanol/water mixture. Dilution of a 1000 ppm water standard in methanol or gravimetric mixing of anhydrous methanol in distilled water gave the desired mixtures. The nominal concentration of SUNY catalyst was $2.5 \times 10^{-3}$ gram moles per liter of the methanol or methanol-water mixture.

Ethylene was chemically scrubbed to remove oxygen using a copper on alumina catalyst/adsorbent giving less than 1 ppm oxygen content in the feed ethylene.

The experiments used the same reaction conditions, namely 50° C., 500 spsig and 2 hours residence time. Results for runs at various amounts of water in methanol are given in Table I below.

TABLE I

| Example No. | Water, ppm | Catalyst Activity |
| --- | --- | --- |
| 1 | 15 | 7971 |
| 2 | 452 | 7658 |
| 3 | 52979 | 7500 |
| 4 | 60115 | 6203 |
| 5 | 105904 | 5148 |
| 6 | 105944 | 4834 |

Table I shows that water was found not to ruin the catalyst activity when the water is used in amounts up to about 10.5% water. Our further data indicates the catalyst activity would likely not drop off too steeply up to water concentrations of about 20 wt %. The Activity column in Table I relates to moles of ethylene reacted per moles of SUNY catalyst in the reaction zone.

Table II below is a summary of data on product distribution by weight percent from runs including those in Table I. The Table II data illustrates a large shift in product distribution, toward lighter oligomers, which we discovered occurred using water in the reaction system.

TABLE II

| Example No. | Water, % | $C_6$ | $C_8$ | $C_{10}$ | $C_{12}$ | $C_{14}$ | $C_{16}$ | $C_{18}$ | $C_{20+}$ |
| --- | --- | --- | --- | --- | --- | --- | --- | --- | --- |
| 7 | ~0[a] | 15.18 | 18.39 | 16.53 | 13.54 | 10.29 | 7.67 | 5.28 | 13.12 |
| 8 | 5[b] | 18.70 | 19.75 | 17.17 | 13.21 | 9.75 | 6.94 | 4.72 | 9.76 |
| 9 | 10[c] | 24.26 | 23.35 | 18.25 | 12.48 | 8.40 | 5.26 | 3.04 | 4.96 |

[a] Mean distribution found in the product alpha olefin (AO) layers from 15 ppm water experiments.
[b] Mean distribution found in the AO layers from Examples 3 and 4.
[c] Mean distribution found in the AO layers from Examples 5 and 6.

Runs were also made with oxygen injected into the reaction zone. We discovered that, unlike water, oxygen was ruinous to the catalyst activity even at low ppm levels. The oxygen ppm amounts are based on the parts by weight of ethylene fed to the reaction zone. The data from several runs where oxygen was injected are summarized in Table III below.

TABLE III

| Example No. | Oxygen, ppm | Catalyst Activity |
| --- | --- | --- |
| 10 | <1 | 8124 |
| 11 | 10 | 6607 |
| 12 | 10 | 7040 |
| 13 | 20 | 6421 |
| 14 | 20 | 5146 |
| 15 | 30 | 4826 |
| 16 | 30 | 4493 |
| 17 | 40 | 2609 |
| 18 | 40 | 3385 |
| 19 | 50 | 699 |
| 20 | 50 | 1044 |

In our initial work, careful measures were taken to exclude water from the reaction zone, such as the purchase of anhydrous methanol and the distillation of the methanol in the presence of sodium to reduce water to a very low level. After we discovered that water was not ruinous to catalyst activity, we explored other variables, such as the effect of pressure. We found surprisingly clean separation of unreacted ethylene from product alpha olefin, even at pressures as high as 500 psig. Table IV below lists results of these runs in Examples 21, 22, 23 and 24. The catalyst solution consisted of the SUNY catalyst (at a concentration of $2.5 \times 10^{-3}$ gram moles per liter of methanol-water solution fed to the reaction zone), methanol and water.

TABLE IV

| Example No. | 21 | 22 | 23 | 24 |
|---|---|---|---|---|
| Run Conditions | | | | |
| Reactor Temperature, °C. | 50 | 50 | 50 | 40 |
| Reactor Pressure, psig | 700 | 600 | 600 | 700 |
| Separator Pressure, psig | 25 | 200 | 500 | 500-300 |
| Catalyst Concentration, Gm/L | | | | |
| Initial Charge | 2.0 | 2.0 | 2.0 | 2.0 |
| Continuous Addition | — | — | — | 20.0 |
| Water Content of Catalyst Solution, Wt % | 10.0 | 10.0 | 10.0 | 10.0 |
| Experimental Results | | | | |
| Overall Length of Run, Hr | 21 | 16 | 16 | 40 |
| Catalyst Productivity, Gm Product/Gm Catalyst | 836 | N/A | N/A | 1127-770 |
| Product Purity, Wt % Alpha-$C_{14}$ | 94.4 | 91.1 | 91.6 | 92.7-94.6 |
| Product Distribution, Epsilon | 0.49 | 0.71 | 0.56 | 0.42-0.31 |

Referring in more detail now to the drawing (graph), the ordinate or "Y" axis relates to product purity, in particular $C_{14}$ linear alpha olefin purity. Impurities in the alpha olefin include branch chain olefins and internal (as opposed to alpha) olefins. The abscissa or "X" axis relates to the product distribution or "epsilon" value. Epsilon is a measure of the extent of reaction and is effectively a ratio of the chain termination rate to the growth rate. It is directly related to the mole fraction, X, of a given carbon number olefin by the following equation:

$$X_r = \epsilon \left( \frac{1}{1+\epsilon} \right)^{r-1}, r \geq 2,$$

where r is the number of ethylene units.

The graph shows the data points, in terms of $C_{14}$ alpha olefin product purity and product distribution, for a number of oligomerization runs made with the above-descirbed SUNY catalyst both with no water (only methanol as a solvent) in the reaction zone and with 10% water in the methanol solvent. As can be noted from the graph, approximately 2% greater $C_{14}$ alpha olefin product purity was achieved with 10% water versus that achieved without water in the methanol. Thus the runs represented by three data points at 0.57 epsilon can be considered. These runs were made at essentially identical conditions except that the run indicated by X had 10% water in the methanol solvent whereas the two runs indicated by the dots had no water in the methanol. The X data point shows about 90.8% purity for the $C_{14}$ alpha olefin whereas the dot data points show about 87.5 to b 88% purity for the $C_{14}$ alpha olefin. The run conditions for the various epsilon values shown on the graph were varied similar to the conditions shown in Examples 21 through 24, except that for the runs indicated by dots, no water was included in the methanol.

What is claimed is:

1. A process for oligomerizing ethylene to normal alpha olefins and recovering said olefins from the reaction product which comprises reacting ethylene in a methanol-water mixture containing 0.5 to 20 wt % water under oligomerization conditions in contact with a nickel ylide defined by the following formula:

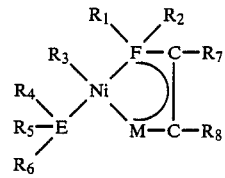

wherein $R_1$, $R_2$, $R_3$, $R_4$, $R_5$, $R_6$, $R_7$ and $R_8$ are either alike or different members selected from the group consisting of hydrogen, alkyl radicals having from about 1 to about 24 carbon atoms, aryl radicals having from about 6 to about 20 carbon atoms, alkenyl radicals having from about 2 to about 30 carbon atoms, cycloalkyl radicals having from about 3 to about 40 carbon atoms, aralkyl and alkaryl radicals having from about 6 to about 40 carbon atoms, halogen radicals, hydroxyl, alkoxy and aryloxy groups, and hydrocarbyl groups carrying halogen, hydroxyl, alkoxy or aryloxy groups, provided that at least one of each $R_1$ to $R_8$ radicals is a sulfonato group or an alkyl, aryl, alkenyl, cycloalkyl, aralkyl or alkaryl carrying a sulfonato group, M is sulfur or oxygen, E is phosphorus, arsenic, antimony or nitrogen and F is phosphorus, arsenic or antimony, to obtain a reaction product containing (A) a methanol-water phase having dissolved therein said nickel ylide and (B) an alpha olefin phase and then separating said phases from each other to recover said alpha olefin phase.

2. A process as defined in claim 1 wherein the percent water is 2 to 15.

3. A process a defined in claim 1 wherein the percent water is 7 to 13.

4. A process a defined in claim 1 wherein the sulfonato group is in $R_4$, $R_5$ and/or $R_6$ and at least one of $R_4$, $R_5$ and $R_6$ is aryl.

5. A process as defined in claim 1 wherein the sulfonato group is in $R_1$, $R_2$ and or $R_3$.

6. A process as defined in claim 1 wherein $R_7$ comprises a sulfonato group.

7. A process as defined in claim 1 wherein E and F are both phosphorus and M is oxygen.

8. A process as defined in claim 4 wherein E and F are both phosphorus and M is oxygen.

9. A process as defined in claim 5 wherein E and F are both phosphorus and M is oxygen.

10. A process as defined in claim 6 wherein E and F are both phosphorus and M is oxygen.

11. A process as defined in claim 8 wherein each of $R_4$, $R_5$, and $R_6$ is phenyl, one of which is substituted with a sulfonato group.

12. A process as defined in claim 11 wherein each of $R_1$, $R_2$, $R_3$ and $R_8$ is phenyl and $R_7$ is hydrogen.

13. A process as defined in claim 9 wherein each of $R_1$, $R_2$ and $R_3$ is phenyl, one of which is substituted with a sulfonato group.

14. A process as defined in claim 13 wherein each of $R_4$, $R_5$, $R_6$ and $R_8$ is phenyl and $R_7$ is hydrogen.

15. A process as defined in claim 10 wherein each of $R_1$, $R_2$, $R_3$, $R_4$, $R_5$, $R_6$ and $R_8$ is phenyl and $R_7$ is a sulfonato group.

16. A process as defined in claim 15 wherein said ylide is in the form of its sodium salt.

17. A process as defined in claim 1 wherein said ethylene and said nickel ylide are contacted at a temperature of from about −20° C. to about 200° C. for about 1 minute to 72 hours.

18. A process as defined in claim 1 wherein said ethylene and said nickel ylide are contacted at a temperature of from about 20° C. to about 100° C. for about 10 minutes to about 24 hours.

19. A process as defined in claim 15 wherein said ethylene and said nickel ylide are contacted at a temperature of from about −20° C. to about 200° C. for about 1 minute to 72 hours.

20. A process as defined in claim 15 wherein said ethylene and said nickel ylide are contacted at a temperature of from about 20° C. to about 100° C. for about 10 minutes to about 24 hours.

21. A process as defined in claim 16 wherein said ethylene and said nickel ylide are contacted at a temperature of from about −20° C. to about 200° C. for about 1 minute to 72 hours.

22. A process as defined in claim 16 wherein said ethylene and said nickel ylide are contacted at a temperature of from about 20° C. to about 100° C. for about 10 minutes to about 24 hours.

23. A process as defined in claim 1 wherein the ethylene pressure is maintained in the range of about 100 to about 2000 psig throughout the reaction.

24. A process as defined in claim 1 wherein the ethylene pressure is maintained in the range of about 350 to about 850 psig throughout the reaction.

25. A process as defined in claim 16 wherein the ethylene pressure is maintained in the range of about 100 to about 2000 psig throughout the reaction.

26. A process as defined in claim 1 wherein the methanol-water phase is recycled to the reaction zone for use therein.

27. A process as defined in claim 13 wherein the methanol-water phase is recycled to the reaction zone for use therein.

28. A process as defined in claim 14 wherein the methanol-water phase is recycled to the reaction zone for use therein.

* * * * *